United States Patent
Halliburton

(10) Patent No.: US 9,089,265 B2
(45) Date of Patent: Jul. 28, 2015

(54) AUTOMATED PARAMETER SELECTION FOR A TOMOGRAPHIC IMAGING DEVICE

(75) Inventor: Sandra S. Halliburton, Shaker Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 575 days.

(21) Appl. No.: 13/350,557

(22) Filed: Jan. 13, 2012

(65) Prior Publication Data

US 2012/0183118 A1    Jul. 19, 2012

Related U.S. Application Data

(60) Provisional application No. 61/432,848, filed on Jan. 14, 2011.

(51) Int. Cl.

| | |
|---|---|
| H05G 1/56 | (2006.01) |
| H05G 1/32 | (2006.01) |
| G05F 1/44 | (2006.01) |
| A61B 6/03 | (2006.01) |
| A61B 6/00 | (2006.01) |
| G05F 1/10 | (2006.01) |

(52) U.S. Cl.
CPC ............... *A61B 6/032* (2013.01); *A61B 6/488* (2013.01); *A61B 6/503* (2013.01); *A61B 6/504* (2013.01); *A61B 6/5211* (2013.01); *A61B 6/542* (2013.01); *A61B 6/544* (2013.01); *G05F 1/44* (2013.01); *H05G 1/56* (2013.01); *A61B 6/469* (2013.01); *A61B 6/545* (2013.01); *G05F 1/10* (2013.01); *H05G 1/32* (2013.01)

(58) Field of Classification Search
CPC .......... H05G 1/08; H05G 1/085; H05G 1/30; H05G 1/34; H05G 1/56; A61B 6/542; A61B 6/545; G05F 1/10; G05F 1/44
USPC ............. 378/16, 91, 101, 109–112, 114–116, 378/901
See application file for complete search history.

(56) References Cited

U.S. PATENT DOCUMENTS

| | | | | |
|---|---|---|---|---|
| 5,103,469 | A * | 4/1992 | Tanaka | 378/16 |
| 6,067,341 | A * | 5/2000 | Horiuchi | 378/8 |
| 6,233,310 | B1 | 5/2001 | Relihan et al. | |
| 7,085,343 | B2 * | 8/2006 | Shinno et al. | 378/9 |
| 7,120,229 | B2 | 10/2006 | Takasawa | |
| 7,215,733 | B2 | 5/2007 | Nabatame | |
| 7,280,635 | B2 * | 10/2007 | Toth | 378/108 |
| 7,542,792 | B2 | 6/2009 | Wollenweber et al. | |
| 7,587,023 | B2 | 9/2009 | Hur | |

(Continued)

OTHER PUBLICATIONS

Winklehner et al., "Automated Attenuation-Based Tube Potential Selection for Thoracoabdominal Computed Tomography Angiography", *Investigative Radiology*, vol. XX, No. X, XXX 2011, pp. 1-7, www.investigativeradiology.com.

*Primary Examiner* — Anastasia Midkiff
(74) *Attorney, Agent, or Firm* — Tarolli, Sundheim, Covell & Tummino LLP

(57) ABSTRACT

Systems and methods are provided for configuring parameters associated with a tomographic scanner. A tomographic scanner is configured to capture a scout image of a patient. A configuration component is configured to determine an average attenuation value representing at least a portion of the scout image and determine each of the tube voltage and tube current for the tomographic scanner from the average attenuation value.

10 Claims, 4 Drawing Sheets

(56) References Cited

U.S. PATENT DOCUMENTS

| | | |
|---|---|---|
| 7,734,006 B2 | 6/2010 | Miyazaki et al. |
| 7,835,496 B2 | 11/2010 | Maschke |
| 2004/0062341 A1 | 4/2004 | Popescu et al. |
| 2004/0086076 A1* | 5/2004 | Nagaoka et al. ............ 378/4 |
| 2007/0116337 A1* | 5/2007 | Toth et al. ............ 382/128 |
| 2008/0240336 A1* | 10/2008 | Miyazaki et al. ............ 378/4 |
| 2010/0183117 A1* | 7/2010 | Tsumuraya et al. ............ 378/9 |

* cited by examiner

AUTOMATED PARAMETER SELECTION FOR A TOMOGRAPHIC IMAGING DEVICE

RELATED APPLICATION

This application claims priority from U.S. provisional patent application Ser. No. 61/432,848, filed Jan. 14, 2011, the entirety of which is hereby incorporated by reference.

TECHNICAL FIELD

The present invention relates generally to the field of medical imaging, and more particularly to systems and methods for automated parameter selection for a tomographic imaging device.

BACKGROUND OF THE INVENTION

X-ray computed tomography, also computed tomography (CT), is a medical imaging method employing tomography created by computer processing. Digital geometry processing is used to generate a three-dimensional image of the inside of an object from a large series of two-dimensional X-ray images taken around a single axis of rotation. CT imaging produces a volume of data that can be manipulated, through a process known as "windowing", in order to demonstrate various bodily structures based on their ability to attenuate the X-ray beam. Although historically the images generated were in the axial or transverse plane, perpendicular to the long axis of the body, modern scanners allow this volume of data to be reformatted in various planes or even as volumetric (3D) representations of structures. Although most common in medicine, CT is also used in other fields, such as nondestructive materials testing and imaging interior portions archaeological relics. Usage of CT has increased dramatically over the last two decades in many countries. An estimated seventy-two million scans were performed in the United States in 2007.

SUMMARY OF THE INVENTION

In accordance with an aspect of the present invention, a computed tomography imaging device is provided. A tomographic scanner is configured to capture a scout image of a patient. A parameter calculation component is configured to determine an average attenuation value representing at least a portion of the scout image and determine the tube voltage and tube current for the tomographic scanner from the average attenuation value.

In accordance with another aspect of the present invention, a computer readable medium is provided that stores machine readable instructions for determining a desired operating voltage and current for an X-ray tube for a scanning procedure using a computed tomography (CT) scanner. The machine readable instructions include a user interface configured to allow a user to specify an associated type of scanning procedure and a voltage determination element configured to select the desired operating voltage for the specified type of scanning procedure according to at least a first descriptive statistic representing attenuation values within a scout image. A current determination element is configured to calculate the desired operating current for the specified type of scanning procedure as a function of at least the extracted first descriptive statistic.

In accordance with a further aspect of the present invention, a method is provided for determining a tube current for a computed tomography (CT) imaging device. A scout image of a patient is obtained at the CT imaging device, the scout image including a region of interest. An average attenuation within the region of interest is determined. A tube voltage is selected from a plurality of available tube voltages according to the attenuation value. A function of the average attenuation is selected from a plurality of available functions according to the selected tube voltage. A tube current is calculated from the selected function of the average attenuation.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Figure 1:
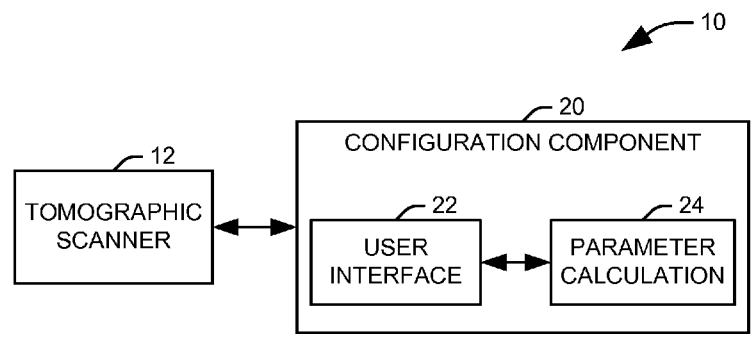
FIG. 1 illustrates a system for imaging a patient in a tomographic scanner in accordance with an aspect of the present invention.

FIG. 1 illustrates a system 10 for imaging a patient in a tomographic scanner 12, for example, a computed tomography (CT) scanner, in accordance with an aspect of the present invention. In accordance with an aspect of the present invention, the system 10 comprises a configuration component 20 that is configured to provide at least one configuration parameter for the tomographic scanner 12. The configuration component 20 can be implemented as dedicated hardware, a software program operating on a general purpose processor, or some combination of both. The configuration component 20 can be part of a control system (not shown) for the tomographic scanner 12 or implemented as a standalone device.

In one implementation, the at least one configuration parameter can include an independent X-ray tube voltage and a dependent X-ray tube current for the tomographic scanner 12. In accordance with an aspect of the invention, each of the X-ray tube voltage and the X-ray tube current for a given scanning procedure can be determined from an associated type of the scanning procedure and one or more appropriate metrics of the patient's size. For example, the associated type of the procedure can be a function of a location within the patient to be scanned, such that various procedure types can include chest imaging, abdominal imaging, neural imaging, imaging of peripheral vascular structures, and specific cardiovascular imaging procedures such as a pulmonary vein imaging procedure, a coronary artery imaging procedure, and an aorta imaging procedure.

The patient size parameter or parameters can be determined from a scout image captured by the tomographic scanner 12. In accordance with an aspect of the invention, the patient size metric can be calculated from the scout image as a descriptive statistic representing the attenuation of the imaging media (e.g., X-rays) during passage through the region of interest. This calculation can be performed at the parameter calculation component 20, although in some implementations it can be performed at the tomographic scanner 12 or another external source and provided to the parameter calculation component via a user interface 22. It will be appreciated that attenuation can be measured at each of a plurality of pixels within the scout image, and the descriptive statistic can include an average measure, deviation measure, or any other appropriate statistic across the plurality of pixels. Examples of measures of average can include the mode, mean, or median of the attenuation values. Examples of measures of deviation can include the variance, standard deviation, range, and interquartile range of the attenuation values. Other possible statistics can include extrema (e.g., minimum and maximum attenuation values), percentile values, and a count or proportion of pixels falling within one or more ranges of interest.

Values for the at least one configuration parameter can be determined at a parameter calculation component 24. The parameter calculation component 24 can comprise an appropriate expert system for determining an appropriate value for the at least one configuration parameter. For example, the parameter calculation component 24 can comprise a rule-based system, a classifier, implemented, for example, as a statistical classifier or neural network, or any similar system configured to receive a plurality of inputs representing the patient's size and the desired scanning procedure and output appropriate values for the at least one parameter. In one implementation, the parameter calculation component 24 is configured as a rule-based system that selects an X-ray tube voltage and a function of an average attenuation based on the provided procedure type and the average attenuation itself and provides an X-ray tube current from the selected function using the average attenuation as an input. The resulting configuration parameters can be displayed to an operator at the user interface 22.

Figure 2:
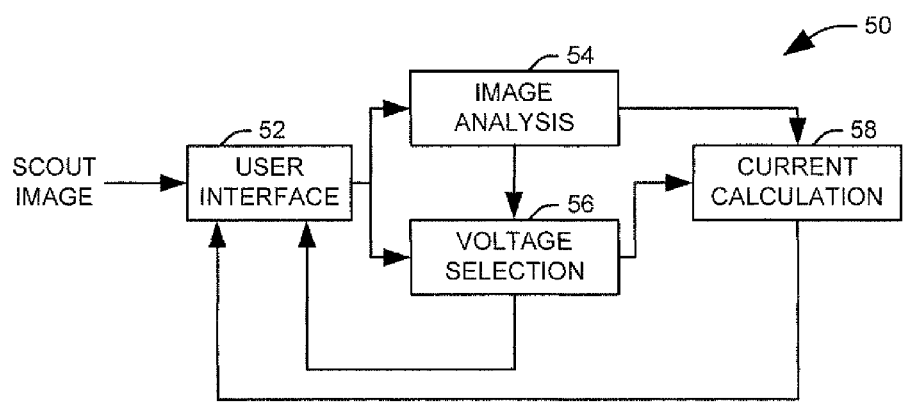
FIG. 2 illustrates one example of a configuration system to provide a tube voltage and a tube current for an imaging procedure at a tomographic scanner in accordance with an aspect of the present invention.

FIG. 2 illustrates one example of a configuration system 50 configured to provide a tube voltage and a tube current for a given imaging procedure performed at a computed tomography (CT) scanner, in accordance with an aspect of the present invention. The illustrated configuration system 50 can be implemented as dedicated hardware, a software program operating on a general purpose processor, or some combination of both, and can be part of a control system for the tomographic scanner or implemented as a standalone device.

The configuration system includes a user interface 52 where an associated type of an imaging procedure can be specified by a user. For example, the user interface 52 can instruct an associated display (not shown) to display one or more options to the user and receive input from an associated input device (not shown) representing the desired procedure type. It will be appreciated, however, that in some implementations, the procedure type can be determined automatically by the configuration system 50 from the tomographic scanner. The associated type of the procedure can be a function of a location within the patient to be scanned, such that various procedure types can include cardiovascular, chest, abdominal, neuro, or peripheral vascular imaging procedures.

An image analysis component 54 can analyze a scout image captured by the tomographic scanner to provide one or more descriptive statistics representing the attenuation of the imaging media (e.g., X-rays) during passage through the region of interest. It will be appreciated that attenuation can be measured at each of a plurality of pixels within the scout image, and the descriptive statistic can include an average measure, deviation measure, or any other appropriate statistic across the plurality of pixels. In the illustrated implementation, a mean attenuation value over the region of interest is used.

A tube voltage for the selected imaging procedure can be determined at a voltage selection component 56 from the one or more descriptive statistics. The voltage selection component 56 can include an appropriate expert system for determining a tube voltage from the one or more descriptive statistics. In the illustrated implementation, the voltage selection component 56 comprises a rule-based system that compares the mean attenuation value to one or more predefined ranges and selects the X-ray tube voltage according to the range in which the mean attenuation value falls.

A current calculation component 58 calculates the tube current for the scanning procedure as a function of the one or more descriptive statistics. In the illustrated implementation, the current calculation component 58 stores a plurality of a linear functions of the mean attenuation, and selects a function for use based on the provided procedure type and the selected tube voltage (which was itself selected according to the value of the mean attenuation). A desired X-ray tube current is calculated from the selected function using the average attenuation as an input. The resulting configuration parameters can be displayed to an operator at the user interface 52.

Figure 3:
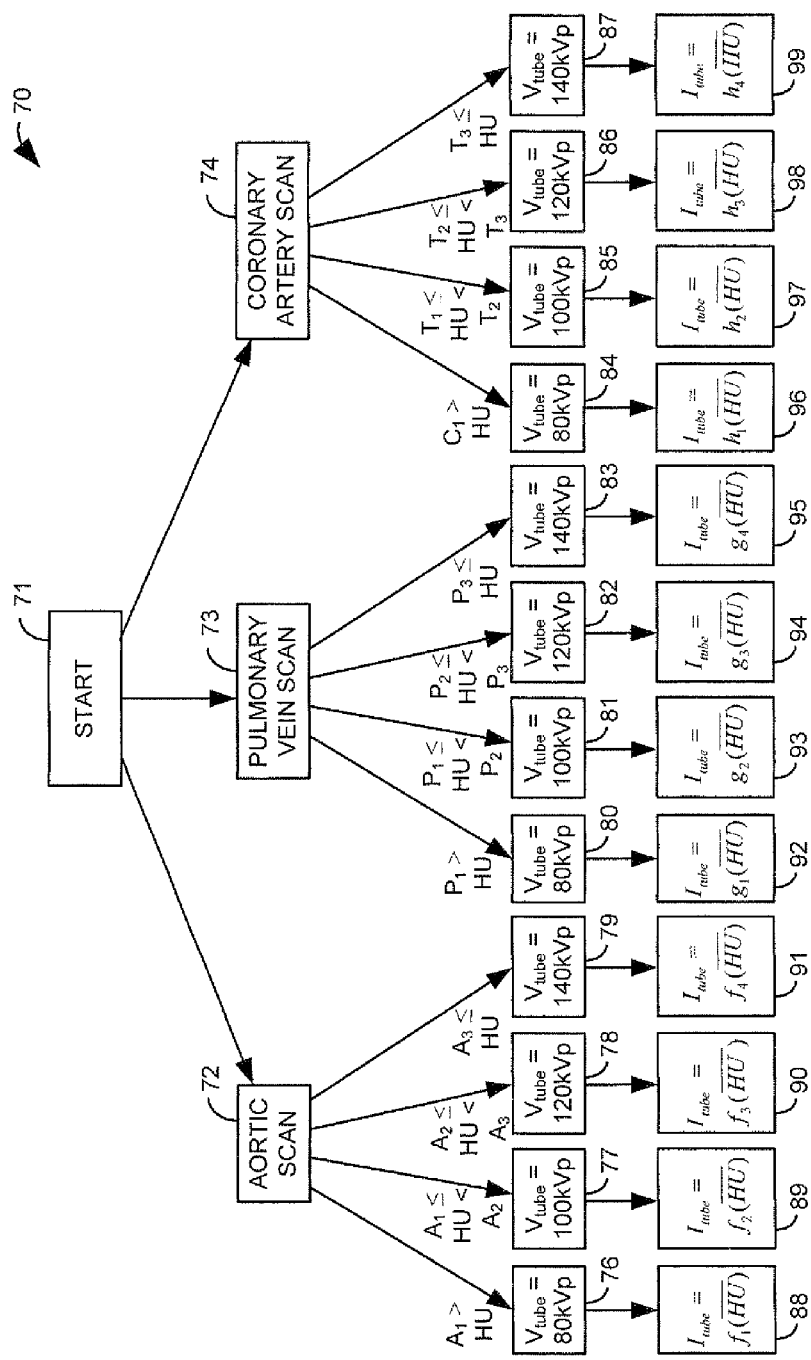
FIG. 3 illustrates a simplified implementation of decision tree that could be employed by a configuration system in accordance with an aspect of the present invention.

FIG. 3 illustrates a simplified implementation of decision tree 70 that could be employed by a configuration system in accordance with an aspect of the present invention. At a first node 71 of the decision tree, one of a plurality of nodes 72-74 representing individual scanning procedure types can be selected. In the illustrated example, the configuration system 70 focuses solely cardiovascular imaging, although it will be appreciated that a practical implementation could contain a variety of procedure types representing various locations within the body.

Although the present invention is not limited to specific values of the tube voltage, for this specific example, common peak voltage values of eighty, one hundred, one hundred twenty, and one hundred forty kilovolts are used for all three procedures. Accordingly, the nodes 72-74 representing the scanning procedures have respective sets of child nodes 76-79, 80-83, and 84-87 representing the four tube voltage values, with an appropriate tube voltage value for each procedure being selected according to a mean attenuation value, $\overline{HU}$, from a region of interest with the scout image. To this end, each procedure has an associated set of threshold values (A1-A3, P1-P3, and C1-C3) defining four distinct ranges of the mean attenuation value. An appropriate tube voltage is selected when the mean attenuation value falls within its associated range.

In the illustrated example, each tube voltage and procedure combination has an associated function of the mean attenuation value ($f_1(\overline{HU})$-$f_4(\overline{HU})$, $g_1(\overline{HU})$-$g_4(\overline{HU})$, and $h_1(\overline{HU})$-$h_4(\overline{HU})$) for calculating a corresponding tube voltago current, represented by a final layer of nodes 88-99. It will be appreciated, however, that in some implementations, each tube voltage and procedure combination can have multiple functions for calculating the tube current, based for example, on subranges of the mean attenuation value, other values derived from the scout image, or one or more characteristics of the patient. In the illustrated implementation, each function is a linear function of the mean attenuation value, and thus the functions associated with a given tube voltage and procedure combination can be represented as a piecewise linear function of the mean attenuation value. It will be appreciated, however, that the functions can include higher order or other non-linear terms, as well as other parameters based on the scout image or patient history.

Figure 4:
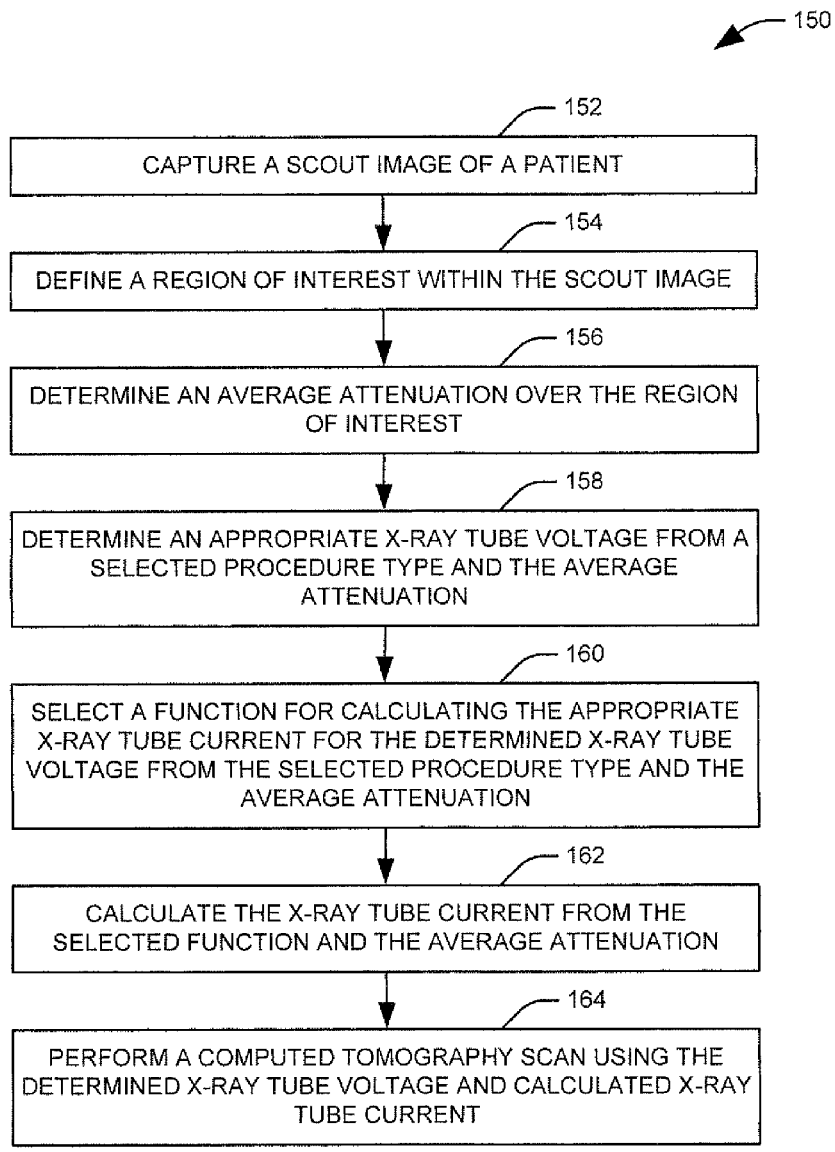
FIG. 4 illustrates an illustrative methodology for determining an X-ray tube voltage and an X-ray tube current for a computed tomography (CT) scan in accordance with an aspect of the present invention.

In view of the foregoing structural and functional features described above, a methodology in accordance with various aspects of the present invention will be better appreciated with reference to FIG. 4. While, for purposes of simplicity of explanation, the methodology of FIG. 4 are shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a methodology in accordance with an aspect of the present invention.

FIG. 4 illustrates an illustrative methodology 150 for determining an X-ray tube voltage and an X-ray tube current for a computed tomography (CT) scan in accordance with an aspect of the present invention. The methodology 150 begins at 152, where a scout image of a patient is captured. At 154, a region of interest within the scout image is defined. At 156, an average attenuation over the region of interest is determined. It will be appreciated that the average attenuation can be provided to an operator by the tomographic scanner.

At 158, an appropriate X-ray tube voltage is determined from a selected procedure type and the average attenuation. In one implementation, when an aorta imaging procedure is selected, a peak X-ray tube voltage of one hundred kilovolts is used when the average attenuation is below a threshold value, and a peak X-ray tube voltage of one hundred twenty kilovolts is used when the average attenuation meets or exceeds the threshold value.

At 160, a function for calculating the appropriate X-ray tube current for the determined tube voltage is selected according to the selected procedure type and the average attenuation. For example, the X-ray tube current can be calculated as a first function of the average attenuation when the average attenuation is below a threshold value and the X-ray tube current can be calculated as a second function of the average attenuation when the average attenuation is above a threshold value. At 162, the X-ray tube current is calculated from the selected function. At 164, a computed tomography scan is performed using the determined X-ray tube voltage and the dependent calculated X-ray tube current.

An illustrative algorithm for an aorta scan procedure, in accordance with an aspect of the present invention, can be represented as:
if HUnorm<40
   x-ray tube voltage=100 kV
   tube current=(HUnorm*3.769)−31.088←This number is then adjusted to be a multiple of 5.
if HUnorm>or=to 40
   x-ray tube voltage=120 kV
   tube current=(HUnorm*2.8037)−35.948←This number is then adjusted to be a multiple of 5.
   where $HU_{norm}$ is an average attenuation value from the scout image.

Figure 5:
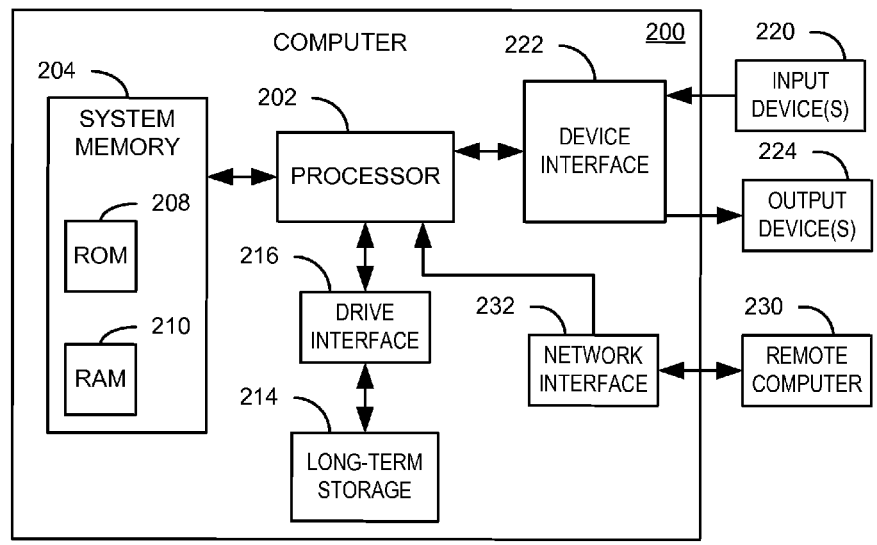
FIG. 5 illustrates a computer system that can be employed to implement systems and methods described herein.

FIG. 5 illustrates a computer system 200 that can be employed to implement systems and methods described herein, such as based on computer executable instructions running on the computer system. The computer system 200 can be implemented on one or more general purpose networked computer systems, embedded computer systems, routers, switches, server devices, client devices, various intermediate devices/nodes and/or stand alone computer systems. Additionally, the computer system 200 can be implemented as part of the computer-aided engineering (CAE) tool running computer executable instructions to perform a method as described herein.

The computer system 200 includes a processor 202 and a system memory 204. Dual microprocessors and other multi-processor architectures can also be utilized as the processor 202. The processor 202 and system memory 204 can be coupled by any of several types of bus structures, including a memory bus or memory controller, a peripheral bus, and a local bus using any of a variety of bus architectures. The system memory 204 includes read only memory (ROM) 208 and random access memory (RAM) 210. A basic input/output system (BIOS) can reside in the ROM 208, generally containing the basic routines that help to transfer information between elements within the computer system 200, such as a reset or power-up.

The computer system 200 can include one or more types of long-term data storage 214, including a hard disk drive, a magnetic disk drive, (e.g., to read from or write to a removable disk), and an optical disk drive, (e.g., for reading a CD-ROM or DVD disk or to read from or write to other optical media). The long-term data storage can be connected to the processor 202 by a drive interface 216. The long-term storage components 214 provide nonvolatile storage of data, data structures, and computer-executable instructions for the computer system 200. A number of program modules may also be stored in one or more of the drives as well as in the RAM 210, including an operating system, one or more application programs, other program modules, and program data.

A user may enter commands and information into the computer system 200 through one or more input devices 220, such as a keyboard or a pointing device (e.g., a mouse). These and other input devices are often connected to the processor 202 through a device interface 222. For example, the input devices can be connected to the system bus by one or several parallel ports, a serial port, or a universal serial bus (USB). One or more output device(s) 224, such as a visual display device or printer, can also be connected to the processor 202 via the device interface 222.

The computer system 200 may operate in a networked environment using logical connections (e.g., a local area network (LAN) or wide area network (WAN) to one or more remote computers 230. A given remote computer 230 may be a workstation, a computer system, a router, a peer device or other common network node, and typically includes many or all of the elements described relative to the computer system 200. The computer system 200 can communicate with the remote computers 230 via a network interface 232, such as a wired or wireless network interface card or modem. In a networked environment, application programs and program data depicted relative to the computer system 200, or portions thereof, may be stored in memory associated with the remote computers 230.

From the above description of the invention, those skilled in the art will perceive improvements, changes, and modifications. Such improvements, changes, and modifications within the skill of the art are intended to be covered by the appended claims.

Having described the invention, I claim:

1. A non-transitory computer readable medium storing machine readable instructions for determining a desired operating voltage and current for an X-ray tube for a scanning procedure using a computer tomography (CT) scanner, the machine readable instructions executable to perform a method comprising:
   allowing a user to specify an associated type of scanning procedure;

selecting the desired operating voltage for the specified type of scanning procedure according to at least a first descriptive statistic representing attenuation values within a scout image; and selecting a function of the first descriptive statistic from desired operating voltage and calculating the desired operating current from the selected function of at least the first descriptive statistic.

2. The computer readable medium of claim 1, wherein the first descriptive statistic is a measure of deviation of the attenuation values across a plurality of pixels within the scout image.

3. The computer readable medium of claim 1, wherein the first descriptive statistic is one of a median, mean, or mode of the attenuation values.

4. The computer readable medium of claim 1, wherein the specified type of scanning procedure defines a location within a body of a patient to be scanned.

5. The computer readable medium of claim 1, wherein the first descriptive statistic represents attenuation values within a region of interest comprising less than the entire scout image.

6. A method for determining a tube current for a computed tomography (CT) imaging device comprising:

obtaining a scout image of a patient at the CT imaging device, the scout image including a region of interest;

determining an average attenuation within the region of interest;

selecting a tube voltage from a plurality of available tube voltages according to the average attenuation;

selecting a function of the average attenuation from a plurality of available functions according to the selected tube voltage; and calculating a tube current from the function of the average attenuation.

7. The method of claim 6, wherein selecting a tube voltage from a plurality of available tube voltages further comprises selecting each of the tube voltages according to a location of the patient to be scanned.

8. The method of claim 6, wherein each of the plurality of functions is a linear function of the average attenuation.

9. The method of claim 6, wherein the average attenuation is a mean attenuation across a plurality of pixels within the region of interest.

10. The method of claim 6, wherein the method is implemented as machine executable instructions stored on a computer readable medium associated with the CT imaging device.

* * * * *